United States Patent [19]

Hagen et al.

[11] Patent Number: 4,532,219

[45] Date of Patent: Jul. 30, 1985

[54] HIGH FREQUENCY RADIATION-INDUCED PLASMA ANALYSIS OF VOLATILE OR NON-VOLATILE MATERIALS

[75] Inventors: Donald F. Hagen, Woodbury; John S. Marhevka, Maplewood, both of Minn.

[73] Assignee: Minnesota Mining and Manufacturing Company, St. Paul, Minn.

[21] Appl. No.: 574,556

[22] Filed: Jan. 27, 1984

[51] Int. Cl.³ ............................................. G01N 31/12
[52] U.S. Cl. ..................................... 436/155; 250/288; 313/231.41; 315/111.41; 356/316; 422/78
[58] Field of Search ...................... 313/231.41, 231.51; 315/111.41; 356/316; 422/68, 78, 98, 21, 22; 436/155, 156, 35; 250/288; 376/143

[56] References Cited

U.S. PATENT DOCUMENTS

| Re. 29,304 | 7/1977 | Greenfield et al. | 356/85 |
|---|---|---|---|
| 3,467,471 | 6/1969 | Greenfield et al. | 356/36 |
| 3,843,257 | 10/1974 | Wooten | 356/85 |
| 3,923,398 | 12/1975 | Adler | 356/85 |
| 4,136,951 | 1/1979 | Macourt | 356/36 |
| 4,225,235 | 9/1980 | Anderson et al. | 356/316 |
| 4,330,295 | 5/1982 | Taylor et al. | 23/230 |

FOREIGN PATENT DOCUMENTS 1368810 10/1974 United Kingdom .

OTHER PUBLICATIONS

"Microwave Induced Plasma", by J. W. Carnahan in *American Laboratory*, 15, 31, (1983).

"Determination of Halogenated Organic Compounds in Water by Gas Chromatography/Atmospheric Pressure Helium Microwave-Induced Plasma Emission Spectrometry with a Heated Discharge Tube for Pyrolysis", by K. Chiba and H. Haraguchi in Anal. Chem., 55, 1504, (1983).

"Microwave Induced Electrical Discharge Detectors for Gas Chromatography", by T. H. Risby and Y. Talmi in *CRC Critical Reviews in Analytical Chemistry*, B. Campbell, ed., CRC Press, Inc., Boca Raton, FL 33431, 1983.

K. S. Brenner in *J. Chromat.*, 167, 365, (1978).

*Primary Examiner*—Barry S. Richman
*Assistant Examiner*—Michael S. Gzybowski
*Attorney, Agent, or Firm*—Donald M. Sell; James A. Smith; Lorraine R. Sherman

[57] ABSTRACT

An apparatus and method for analyzing a sample of an inorganic or organic material, wherein the sample is in a discharge tube within a plasma cavity interfaced to an analytical device and a high frequency-sustained radiation-induced excitation plasma is initiated and sustained in the plasma cavity, which plasma is capable of causing the sample to pyrolyze and emit radiation, which emitted radiation or resulting atomic and molecular constituents may be analyzed, the improvement comprising:
  means for fixing or immobilizing the sample at a position spaced apart from the plasma, and
  means for elongating the plasma so as to cause it to encompass the sample.

20 Claims, 12 Drawing Figures

FIG.8A

HIGH FREQUENCY RADIATION-INDUCED PLASMA ANALYSIS OF VOLATILE OR NON-VOLATILE MATERIALS

TECHNICAL FIELD

The present invention relates to an analytical method and apparatus for the qualitative and quantitative determination of volatile and non-volatile materials using a high frequency radiation-induced plasma.

BACKGROUND ART

Tremendous strides have been made in the field of analytical chemistry in recent years. Conventional "wet" chemical analysis which is slow and laborious suffers from a large number of variables that can be present in the physical procedures involved, and has been largely replaced by more sophisticated techniques. One such technique involves the spectral analysis of particles that are introduced directly into a plasma. The high temperature and high energy conditions prevelant in the plasma cause molecules and atoms to emit their characteristic spectra which can be readily identified.

Plasmas of excited gases are generated by a variety of means including chemical flames, arc- or spark-discharges, inductively coupled radio frequency, and microwave-sustained gas discharges using excitation gases such as argon, helium, nitrogen, or oxygen.

While high energy plasmas are used to excite atoms and molecules to an emissive condition, a specific advantage of a helium plasma is that it has sufficient energy to generate principally atomic emission spectra for the elements present in the sample. A helium plasma device known as a microwave-sustained emission detector has recently been employed to great advantage for qualitative and quantitative gas chromatographic analysis.

Recent publications on microwave plasma spectroscopy include "Microwave Induced Plasma" by J. W. Carnahan in *American Laboratory*, 15, 31–36 (1983), "Determination of Halogenated Organic Compounds in Water by Gas Chromotagraphy/Atmospheric Pressure Helium Microwave-Induced Plasma Emission Spectrometry with a Heated Discharge Tube for Pyrolysis" by K. Chiba and H. Haraguchi in *Anal. Chem.*, 55, 1504–1508 (1983), and "Microwave Induced Electrical Discharge Detectors for Gas Chromatography" by T. H. Risby and Y. Talmi in *CRC Critical Reviews in Analytical Chemistry*, B. Campbell ed., CRC Press, Inc., Boca Raton, FL, 33431, 1983, 231–265. A commercially available microwave plasma detector (MPD) is a combination of a microwave plasma and a grating spectrometer and limits of measurement and examples of application are described by K. S. Brenner in *J. Chromat.*, 167, 365–380 (1978).

Elemental analysis of volatilized substances can be accomplished using a microwave emission detector (MED), which is also known in the art as a microwave plasma detector (MPD), a microwave-induced plasma detector (MIP), and a helium microwave-sustained emission detector (He MED) where helium is the plasma gas.

Elemental analyses using a microwave plasma detector wherein volatile particulate or gaseous samples are transported in a carrier gas to a plasma are disclosed in U.S. Pat. Nos. 4,225,235, 3,923,398, 3,843,257 and British Pat. No. 1,368,810. U.S. Pat. No. 4,136,951 discloses use of a dual plasma system and here also a vaporized sample is transported in a carrier gas from a pyrolysis plasma to a secondary plasma which is spectrally analyzed.

U.S. Pat. No. 4,330,295 discloses the coating of a polymer solution onto a quartz capillary tube or use of an organic sample in a solid form such as a film, filament, or small bead, subjecting the sample to a microwave discharge to decompose and volatilize it, then transporting the decomposed fragments by means of a carrier gas for subsequent separations and determinations. In this reference, the plasma and plasma-containing energized fragments were not subjected to direct analysis; instead they were transported to another analytical device for analysis.

A key weakness in state-of-the-art MED units is the method of sample introduction. When samples are easily volatilized and precautions are taken to minimize conduit (wall) interactions, atomic emission of the sample gives a quantitative representation of the elements or elemental ratios present in the sample. For example, volatile components, separated from a gas chromatograph, can be transported from the gas chromatograph to the excitation plasma of an MED unit by means of a heated conduit, such as glass-lined stainless steel capillary tubing, and present little if any problem. However, volatile samples comprise only a small portion of the many materials subject to analysis using an MED. A widely utilized means for volatilizing organic compounds involves pyrolysis or fragmentation to smaller more volatile entities, which are then transported by means of a carrier gas through heated conduits to the excitation plasma.

Use of a carrier gas to transport particles to and from the plasma results in certain shortcomings. Particulate fragments frequently recombine or condense on the conduit walls or are absorbed on the walls of the pyrolysis chamber and transporting conduit. The results in loss of material and "ghosting", that is, materials sorbed onto conduits (commonly referred to as transfer lines), interface surfaces, sample probes, valves and the like may be introduced into the MED during subsequent sample analysis and can lead to spurious, erroneous analytical results. This loss of part of the sample and the difficulty in maintaining reproducible pyrolysis temperatures and other conditions make it difficult to obtain quantitative and reproducible results. It is virtually impossible to completely volatilize most organic polymers by pyrolysis without losing fractions to the walls of the pyrolysis apparatus and to the transporting conduit.

A technique in common usage in the background art is to aspirate and atomize or nebulize non-volatile material into a plasma. When materials are introduced to a plasma by apsiration, nebulization, atomization, and the like, more subtle deficiencies are noted. For example, when an aerosol reaches a plasma, the aerosol may absorb energy from that plasma and as a result, may seriously affect plasma operating conditions and performance. In an extreme case, sample introduction may overload the plasma sufficiently to extinguish it. None of these devices or techniques utilizing solvent aerosols for the introduction of non-volatile liquids or solids can be used with a helium MED since the elements in the solvent constitute an interference with the determination of the elements present in the sample.

To overcome the disadvantages of transporting particles and vaporized samples to a plasma in a carrier gas, some efforts have been directed to sample introduction directly into a plasma, as for example in U.S. Pat. No. 3,467,471 and Re. 29,304. However, the shortcomings such as incomplete fragmentation, irreversible absorption of fragments on the conduit, and the possibility that too much sample, especially in powder form, may extinguish the plasma, are not overcome.

SUMMARY OF THE INVENTION

The present invention overcomes shortcomings of the prior art which generally teach the introduction of a volatilized sample into a plasma cavity by means of a carrier gas. In contrast to these prior art teachings, the present invention provides a method and apparatus therefor which includes introduction of a non-volatile sample into a plasma cavity of a plasma detector device and transporting the plasma to the sample.

Briefly, the present invention provides an apparatus for analyzing a sample of an inorganic or organic material, wherein the sample is in a discharge tube within a plasma cavity interfaced to an analytical device and a high frequency-sustained radiation-induced excitation plasma is initiated and sustained in the plasma cavity, which plasma is capable of causing the sample to pyrolyze and emit radiation, which emitted radiation or resulting atomic and molecular constituents may, optionally, be analyzed,
the improvement comprising:
  means for fixing or immobilizing the sample at a position spaced apart from the plasma, and
  means for elongating the plasma so as to cause it to encompass the sample.

In addition, the present invention provides a method of analysis of inorganic and organic material comprising the steps of:
(a) providing an immobilized sample of the material in a gas atmosphere in a plasma cavity interfaced to an analytical device,
(b) initiating a high frequency sustained radiation-induced excitation plasma spaced apart from the sample,
(c) causing the plasma to elongate and encompass the sample for a length of time and at an energy level sufficient to pyrolyze the sample and cause it to emit radiation, and
(d) optionally, analyzing the emitted radiation.

In another aspect, the present invention teaches the use of multiple plasmas. An initial, chaser or primary plasma may be used and optionally enlarged to volatilize and transport the sample into a second excitation plasma. It is also possible to extend the secondary plasma and cause it to move toward the chaser plasma. The plasmas may be two or more distinct zones or be caused to fuse into one zone. The effective power applied to the two plasmas may be the same or different. In all cases, the excitation plasma is spaced apart (in the range of 0.1 cm to 10 cm) from the sample. At least one of the plasmas can be caused to move towards the sample and encompass it so that the sample can be analyzed, for example by spectral means.

By controlling, adjusting, and manipulating the power applied to the plasma cavity the plasma or multiple plasmas can be made to encompass the entire sample; this obviates or minimizes adherance of sample or sample fragments to the discharge tube wall, and allows quantitative analysis. In the alternative, the plasma or multiple plasmas can be made to encompass the sample by manipulation of the gas pressure inside the discharge tube. There is no need for a massive heat reservoir as compared to samples which in the prior art were aspirated into the plasma cavity. The portion of the discharge tube where the sample is located can be cleaned and residues can be atomized by the high temperature plasma gases, thus avoiding ghosting or carry-over in subsequent sample analysis.

This invention provides for analysis of volatile and non-volatile substances with a superior method of atomizing and exciting a sample in a plasma. Earlier devices have dealt with transporting the sample, in some manner, to the excitation plasma. Accompanying shortcomings of this procedure have been mentioned such as loss of sample due to wall or conduit effects, inability to handle non-volatile materials, and inability to sustain a plasma. In the present invention, problems associated with transporting samples, sample fragments, and interfering aerosols into the excitation plasma are eliminated.

Analysis of non-volatile and inorganic samples which heretofore were difficult or impossible to analyze by conventional MED techniques is now possible by practice of this invention. Organic polymers, salts of organic polymers, and even inorganic substances such as sodium chloride can be successfully analyzed for a constituent element or elements.

In this application:
"analytical device" means an instrument which provides qualitative and quantitative data;
"plasma" means an ionizing high energy gas that is emitting energy such as light and operating at temperatures up to 15,000° C. (thermodynamic temperature);
"plasma cavity" means a region of space within which conditions are optimized for the generation and maintenance of a plasma;
"microwave plasma cavity" means the locus where microwave radiation is sustained and the microwave energy has a frequency greater than 300 MHz, preferably about 912 or about 2450 MHz;
"sample" means a solid, a high boiling liquid, or a solvent-soluble material;
"discharge tube" means a high temperature-stable tube (e.g., quartz or ceramic) within which a plasma is located;
"sample zone" means a region in a discharge tube where a sample is located;
"plasma plume" means a elongated region of space occupied by a plasma;
"pyrolysis" means decomposition of a material into fragments including atomic and molecular species utilizing high temperature and/or high energy; and
"non-volatile sample" means a solid or liquid having a vapor pressure less than 0.1 mm of Hg at 400° C.

BRIEF DESCRIPTION OF THE DRAWING

In the accompanying drawing.

DETAILED DESCRIPTION

In a preferred embodiment, the present invention provides an analytical method for a volatile or nonvolatile substance comprising the steps of:

(a) providing an immobilized sample of the substance within a plasma cavity of a microwave-induced plasma detector having a variable power supply and an analytical device such as an optical or mass spectrometer, the cavity having therein a gas atmosphere suitable for the generation and maintenance of a plasma at a pressure in the range of 1 to 760 mm of Hg, preferably 1 to 5 mm of Hg, (b) initiating and sustaining a microwave-induced plasma in the plasma cavity in which the plasma is spaced apart from the sample by a distance of 0.1 to 10 cm, the power to the plasma cavity being in the range of 1 to 30 watts, (c) manipulating and controlling the power to supply sufficient power to the plasma cavity to elongate the plasma to encompass the sample (preferably in a higher range of 50 to 500 watts), the plasma being an excitation plasma, (d) maintaining the plasma at the higher power range for a time period sufficient to pyrolyze the sample into atomic and molecular constituents and excite the constituents so as to cause them to emit radiant energy, the time period preferably being in the range of 0.01 to 300 sec., and (e) analyzing the resulting atomic and molecular constituents or their emission spectra.

In the method of the present invention, the substances to be analyzed can be volatile materials or they can be solid or highly viscous materials such as inorganic compounds and polymers, e.g., inorganic salts or adhesives. The sample may be immobilized on a probe or on an indentation or shelf in the cavity wall, which wall preferably is ceramic, quartz, or silica, in a plasma discharge tube. The sample is spaced apart from a plasma, the space between the plasma and sample being in the range of 0.1 mm to 10 cm and preferably 0.5 mm to 5 cm. The amount of sample used is dependent on the capacity of the particular plasma used. Less than 5 micrograms, preferably less than 1 microgram, is a convenient quantity. Any plasma may be used in the present invention such as an inductively-coupled plasma having a frequency range of 3 to 150 MHz, or a direct current plasma, but preferably the plasma is induced with microwave energy having a frequency range greater than 300 MHz, but preferably having a frequency of approximately 912 or 2450 MHz.

In the method of the present invention, after the sample is immobilized directly in a plasma discharge tube an inert gas such as helium or argon, or a gas such as nitrogen or oxygen is introduced as the excitation gas for the plasma. Helium is the preferred inert gas because of its high ionization energy. High frequency energy with a power suppply setting at a minimum creates and sustains a plasma so that the plasma plume does not touch or engulf the sample in the discharge tube. As mentioned above, the plasma is spaced apart from the sample. The energizing process can be carried out at atmospheric pressure or at reduced pressures. By controlling, adjusting, and manipulating the amount of power applied to the plasma in the plasma cavity, the plasma is caused to elongate and envelope the sample. Elongation of the plasma results in the plasma being transported to the sample. The resulting high temperature and high energy region which encompasses the sample causes sample degradation into fragments which may be molecular or atomic constituents. The plasma provides a high temperature, high energy path which preferably is directed to an optical viewing port in the discharge tube for viewing, for example, in a spectrometric device. Definitive spectral lines or bands can be isolated by a suitable monochromator. Emission intensity of the spectral line(s) or band(s), which is a function of the concentration, can be measured by a photomultiplier detector or other electronic read-out devices. A reference channel in the electro-optical portion of the instrument can be used for stabilization or to null-out background or undesirable interfering spectral lines. Furthermore, a multichannel optical system can be used to observe a number of different spectal lines at the same time, thus detecting different emission lines of the same element or lines of a number of different elements simultaneously.

Also, the plasma can be caused to encompass the sample in a wall-less system. The plasma need not be confined within a quartz tube but may be generated and moved as a torch to a sample in a cavity.

In a preferred embodiment, a multifunctional, multimode, selective, commercially available, microwave-excited emission detector (MED) which is described, for example, in U.S. Pat. No. 3,843,257, is utilized which is capable of detecting and analyzing metallic and non-metallic compositions of inorganic and organic nature in subnanogram amounts on an integrated or real time basis. The detector utilizes microwave energy at high frequencies, for example 2450 MHz (megahertz), to maintain a plasma which, in turn, leads to spectral emission of atomic and polyatomic constituents of the composition being analyzed.

Figure 1:
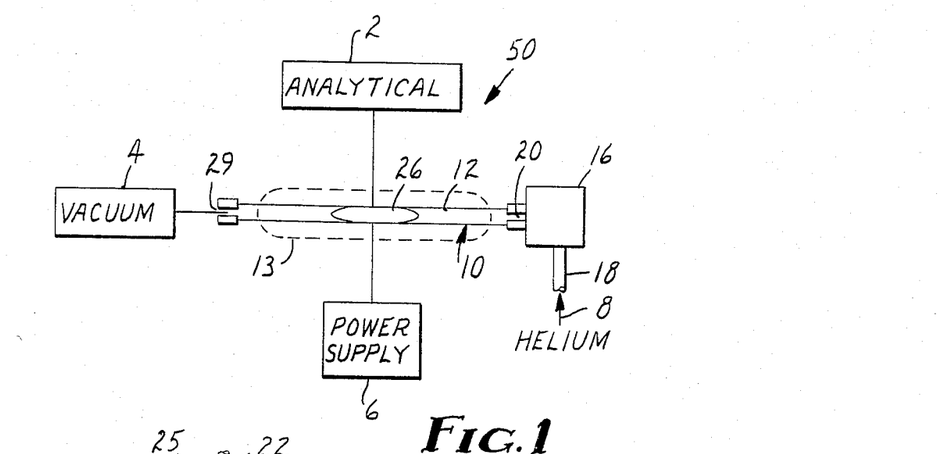
FIG. 1 is a schematic outline of one embodiment of the present invention showing a microwave induced plasma emission detector.

Referring to FIG. 1, a schematic outline of a high frequency radiation-induced emission detector 50 is shown. Discharge tube 10, which can be made of sapphire, alumina, quartz, or other high temperature-stable material, but is preferably a quartz tube within microwave plasma cavity 13. An excitation gas which preferably is helium 8 enters discharge tube 10 through entrance port 20. Pressure inside discharge tube 10 is maintained at exit port 29 by means of vacuum pump 4. Microwave-induced plasma 26 is initiated and maintained by power supply 6 to microwave plasma cavity 13. An analytical instrument 2, such as a spectrometer or other light measuring device, allows establishment of a baseline due to background emissions and can provide an optical read-out when an energized sample is present.

Figure 2:
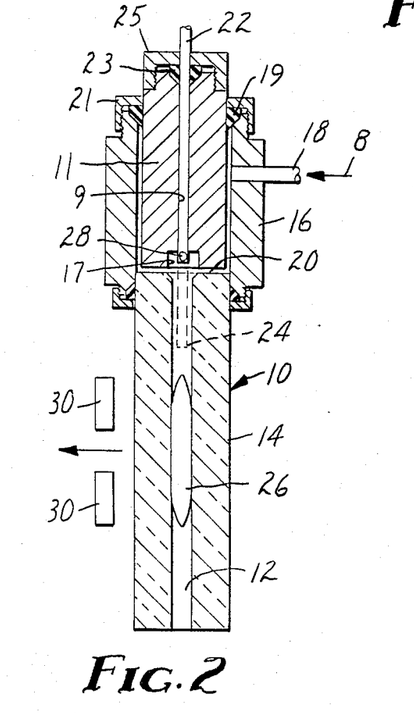
FIG. 2 is an enlarged cross-sectional view of the discharge tube of the microwave induced plasma emission detector of FIG. 1.

FIG. 2 shows an enlarged cross-sectional view of discharge tube 10 of one embodiment of the present invention utilizing as an optical read-out device a microwave-induced emission detector. Discharge tube 10 has quartz walls 14 connected to inlet block 16 which may have fittings made of stainless steel, polyimide, or graphite which include gas inlet 18 and entrance port 20 through which helium gas 8 enters. The microwave power from the microwave power supply 6 (as shown in FIG. 1) is off. Capillary tube 22 which preferably is a precleaned fused silica capillary tube with one end sealed is loaded with sample 28 as follows: Concentric tube 11 having hollow central core 9 is removed from inlet block 16. Capillary tube 22 is extended through concentric tube hollow central core 9 and concentric tube recess 17 and about 1 microgram (μg) of sample 28 which preferably is in solution is deposited on the tip of capillary tube 22. Solvents are removed by evaporation. Sample-loaded capillary tube 22 is withdrawn into recess 17, and concentric tube 11 containing sample-loaded capillary tube 22 therein is connected to inlet block 16 by means of seal 19 and fastening means 21 which may be a nut. Sample-loaded capillary tube 22 is then extended into interior 22 of discharge tube 10 to location site 24 and locked into position by means of seal 23 and fastening means 25 which may be a nut. At this time, the pressure in the interior 12 of discharge tube 10 is reduced to an operating pressure, i.e., about $4 \times 10^2$–$7 \times 10^2$ Pa (3–5 mm Hg) by activation of an instrument attached vacuum pump (as shown in FIG. 1). The microwave power supply (not shown) can be adjusted to supply a minimum amount of energy and plasma 26 can then be ignited by means of a Tesla coil (Edwards High Vacuum, Crawley, Sussex, England).

When power, controlled by the power supply, is decreased to a minimum level, plasma 26, which is constrained in quartz discharge tube 10, decreases in geometric length, and not in ionization energy. A minimum power level is about 1 to 30 watts. At this lower power setting, sample 28 is positionally at least one millimeter, preferably at least one centimeter away from the plasma plume or plasma zone and only radiant energy reaches sample 28. Thus, sample 28 is relatively cool, and it does not fragment; hence there is little or no sample emission but background emission may be present. Mask 30 allows any emitted light to enter a spectrometer or other light measuring device (not shown) oriented perpendicular to the axis of discharge tube 10, although in other embodiments it may be oriented axially to allow establishment of a baseline due to background emissions.

Probe (capillary tube 22) can be a fused silica tube, sealed at one end, and is commercially available, for example, from Hewlett-Packard, Avondale, PA. Quartz capillary tubes or ceramic material can be used as well. In fact any glass or ceramic material, for example fibers which are sufficiently temperature-stable and are essentially non-emissive under plasma conditions are suitable for supporting a sample. For example, a ceramic sample probe made from ceramic fibers as described in U.S. Pat. No. 3,795,524 may be used.

Capillary tubes can be purchased and used in a variety of wall thicknesses and overall diameters; a capillary tube of 0.25 mm outer diameter is especially useful in the present invention.

The length of the sample-containing fused silica capillary tube (probe) 22, which is inserted into the upper portion of discharge tube 10 of FIG. 2 is dependent on the configuration and size of the microwave plasma cavity 13. The length of probe 22 should be sufficient so it can penetrate to location site 24.

Probe 22 is prepared for accepting sample 28 by insertion into discharge tube 10 and elevating the power to clean probe 22 and discharge tube 10.

Figure 3:
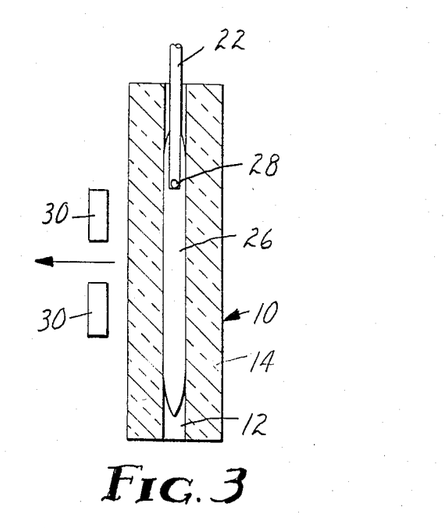
FIG. 3 is an enlarged cross-sectional view of the lower portion of the discharge tube of FIG. 2 subsequent to elongation of the plasma.

FIG. 3 shows discharge tube 10 of FIG. 2 after the power supply (not shown) setting is increased, so that the length of the plasma 26 is increased such that it expands, contacts, and envelopes the sample 28-containing probe 22 at location site 24 (see FIG. 2) within discharge tube 10. An increased power level can be about 150 to 200 watts; however, higher wattages, for example, 500 watts, can be applied. In the presence of helium gas in the interior 12 of discharge tube 10, this increase in power level causes plasma 26 to lengthen and results in plasma 26 enveloping sample 28 and providing it with a continuous high temperature, highly energetic path away from the sample origin to mask 30 and to the optical read-out portion of a spectrometer (not shown) or other electro-optical read-out portion of the instrument.

As a result, sample 28 undergoes complete pyrolysis within high temperature, high energy plasma 26, and at the atomic level the atoms are excited to the emissive state for subsequent analytical measurement, which is usually accomplished by an emission spectrometer or other electro-optical read-out device.

Figure 4:
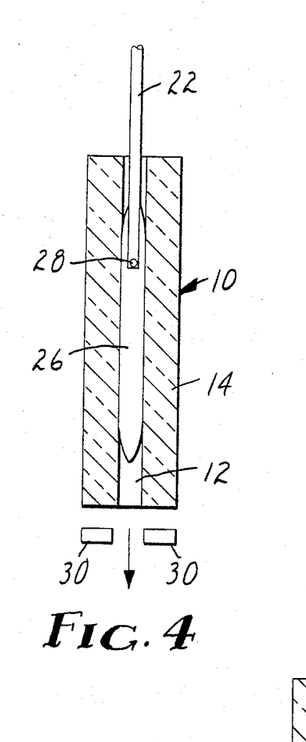
FIG. 4 is an enlarged cross-sectional view of a portion of the discharge tube of FIG. 2 where the emitted light is viewed axially subsequent to elongation of the plasma.

FIG. 4 shows a variation of an alignment of the device components wherein the interior 12 of quartz discharge tube 10 of FIG. 2 is lined up axially with a spectrometer (not shown) to allow a maximum amount of emitted light to pass by mask 30 and enter a spectrometer or other suitable measuring device.

Figure 5:
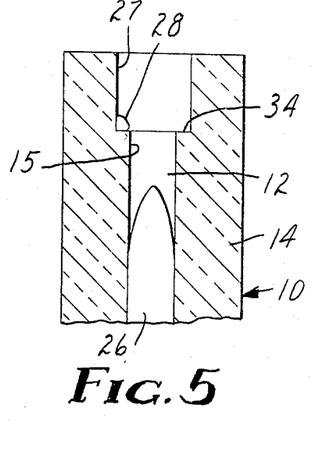
FIG. 5 is an enlarged cross-sectional view of a portion of a modification of the discharge tube of FIG. 2 with an indentation in the inside wall.

Referring to FIG. 5, another embodiment of the present invention is shown in which another method for introducing a sample 28 into interior 22 of discharge tube 10 of an MED is described.

With the power supply turned off, sample 28, about 100 ng, dissolved or dispersed in about one to two microliters of a suitable volatile solvent is deposited in a depression 27 of inside wall 15 (for example, on a provided lip or ledge 34) of the quartz discharge tube 10 which will subsequently contain plasma 26. Sample 28 is deposited at a distance, preferably at least one centimeter, from where the top of the plasma 26 is to be located as determined in a previous control run wherein the power supplied is maintained at a low setting during that control run. Power is then applied at a low setting similar to that in the control. Plasma 26 is then ignited and sustained in the usual manner. This allows for a baseline background emission determination. Thereafter the power is raised to the level indicated earlier to cause the high energy plasma 26 to engulf and pyrolyze sample 28 directly at the discharge tube 10 wall surface 15.

This embodiment is especially suitable for samples which are solid and which are not soluble or are difficultly soluble in solvents which preclude depositing the sample on a probe. It can also be useful to deposit a solution of a sample on the discharge tube wall surface. This method is feasible for solids, polymers, and intractable materials heretofore not suitable for analysis by, for example, the microwave plasma emission technique.

In this method, discharge tube 10 is slightly modified to accommodate the physical placing of a sample. Either a slight depression 27 in inside wall 15 provides lip 34 or lip 34 can be glass-blown into the inside wall 15 of discharge tube 10 to receive sample 28. The depth of such a depression, ledge, or lip 34 is usually in the order of 0.1 mm. Plasma excitation and analysis are conducted in the usual way.

Figure 6:
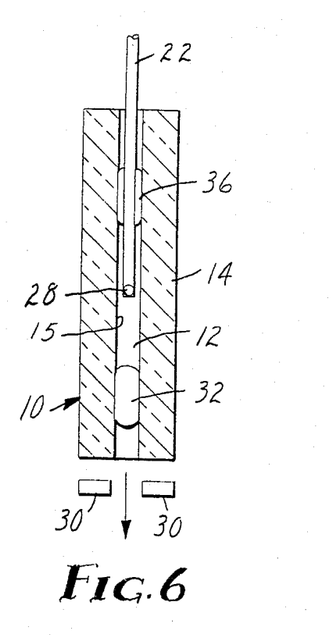
FIG. 6 is an enlarged cross-sectional view of a portion of a discharge tube of a second embodiment of the present invention utilizing dual plasmas.

Referring to FIG. 6, another embodiment of the present invention utilizing dual plasmas is shown. Sample 28 is deposited from solution onto inside discharge tube wall 15 or on probe 22 at the intersection point of two plasmas 36 and 32 when maximum power is applied. That is, there are two plasmas 36 and 32 generated within discharge tube 10. Plasma 36, farthest away from mask 30 of the detector unit, is the "chaser" plasma while plasma 32, closest to mask 30, is the "excitation" plasma. Optionally, as the length of "chaser+ plasma 36 increases, it fuses, near the locus of sample 28, into one plasma, and in a sense, chases sample 28 into excitation plasma 32 concomitantly forming one extended excitation plasma. The resultant atoms are excited to an emissive state. The emitted light passes by mask 30 and enters a spectrometer or other suitable light measuring device (not shown) which as noted above can be axially or perpendicularly oriented.

This dual plasma within the discharge tube is generated as taught in British Pat. No. 1,368,810.

The advantage of multiple plasmas and, optionally, a resultant fused single plasma, is that the sample volatiles cannot diffuse back into a region of lower temperature where sample and sample fragments could condense; that is, wall or conduit effects are eliminated.

While the preferred embodiments of this invention relate to MED, it will be obvious to those skilled in the art that the plasma decomposition products can be analyzed by any other suitable or ancillary analytical technique.

TABLE I describes a variety of organic polymers, salts of organic polymers and an inorganic salt, sodium chloride, which can be analyzed by MED for the elements indicated according to the teachings of this invention.

TABLE I

| MED Analysis of Organic and Inorganic Samples | | |
|---|---|---|
| Sample | Source | Elements |
| Poly(vinyl chloride)[1] | 3M (St. Paul, MN) | C, Cl, H |
| Poly(vinyl p-toluene sulfonate, sodium salt)[2] | 3M (Ferrania, S.p.A., Italy) | C, H, S |
| Viton ™ S363 H | E. I. duPont de Nemours & Co., Inc. (Wilmington, DE) | Br, C, F, H |
| Viton ™ B | E. I. duPont de Nemours & Co., Inc. (Wilmington, DE) | C, F, H |
| Fluorel ™ | 3M (St. Paul, MN) | C, F, H |
| Polysulfone | Cellomer Associates, Inc. (Webster, NY) | C, H, S |
| Sodium Chloride | Matheson, Coleman, and Bell, (Gibbstown, NJ) | Cl, Na |

Figure 7A:
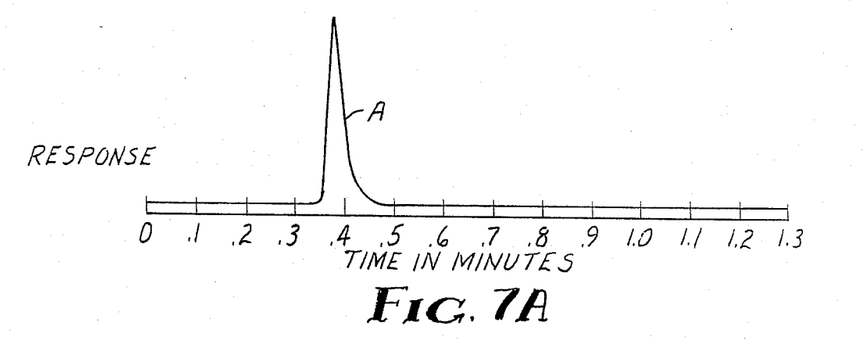
FIGS. 7A, 7B, and 7C are data acquistion system graphs for polyvinyl chloride (see EXAMPLE 1)
Figure 7B:
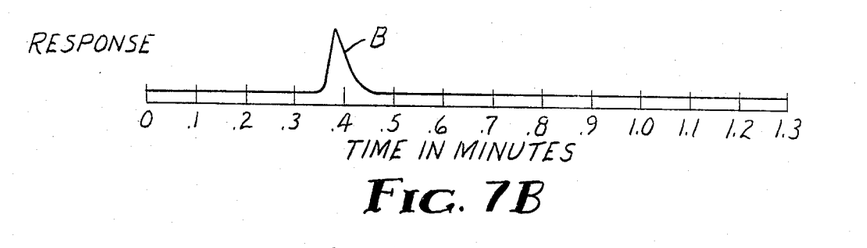
Figure 7C:
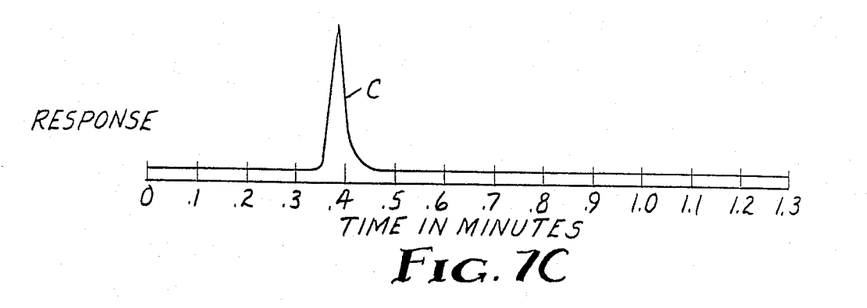

[1]See Example 1. FIGS. 7A, 7B, 7C
[2]See FIGS. 8A, 8B, 8C

The present invention provides a means of qualitative and quantitative atomic and molecular analysis of liquid or solid, volatile or non-volatile samples including certain inorganic and polymeric materials which were heretofore difficult to analyze by conventional means. In the method of the invention the sample is completely pyrolyzed in a single plasma or in multiple plasmas, and the conduit to the plasma cavity is eliminated as a source for fragmentation, condensation, or interaction. The elemental, emission analysis is both quantitative and reproducible.

Objects and advantages of this invention are further illustrated by the following examples, but the particular materials and amounts thereof recited in these examples, as well as other conditions and details, should not be construed to unduly limit this invention.

EXAMPLE 1

The probe, a piece of precleaned, fused silica capillary tube (Hewlett-Packard, Avondale, PA) with one end sealed was inserted into the discharge tube within the cavity of a conventional microwave-excited emission detector (MED) (Applied Chromatography Systems, Ltd., Luton, England) with helium as the excitation gas for the plasma. The discharge tube was specifically designed for operation as described in FIG. 2 above. The power supply of the MED was electrically activated. The plasma, under a reduced pressure of about 4–5 mm Hg, was then ignited by means of a Tesla coil (Edwards High Vacuum, Crawley, Sussex, England) and the power was maintained or reduced to a minimum value such that the emission baseline remained stabilized. Thereafter, the power was stabilized at about 20 watts and the plasma was extinguished by switching off the applied power. The vacuum pump was switched off and the probe was removed from the discharge tube. A thin film of polyvinyl chloride (PVC) (3M, St. Paul, MN) was deposited onto the probe by placing one microliter (1 μl), which contained 466 ng of PVC in tetrahydrofuran (THF) solvent, onto the tip of the fused silica capillary tube and allowing the solvent to evaporate.

The sample-containing probe was reinstalled into the discharge tube and the vacuum was again applied. When a pressure of 4–5 mm Hg was attained, the plasma was reignited and maintained at a power level of 20 watts.

A data acquisition system, comprised of computer, integrator, strip chart recorders, and the like, was activated and a pre-pyrolysis baseline on the MED was monitored for 0.3 minute at the previously determined and set reduced power level. At the end of this time, the applied power was rapidly increased to 120 watts, after which the plasma expanded and engulfed the sample-containing probe. The carbon, hydrogen, and chlorine emission channels of the emission spectrometer unit all gave a rapidly rising peak at 0.35 minute in response as the plasma engulfed the probe as shown graphically in FIGS. 7A, 7B, 7C for carbon (A), hydrogen (B), and chlorine (C), respectively. Response of the emission channels all returned to a flat baseline at 0.45 minute when the sample was completely consumed. Analysis was continued for a sufficient period of time to establish the new baseline at the 120 watt power level setting.

Using the data acquisition system, the relative integrated area responses obtained for each element detected was indicative of the weight of that element present on the probe. Furthermore, the ratios of carbon to hydrogen and carbon to chlorine were indicative of the polymer composition.

EXAMPLE 2

Figure 8A:
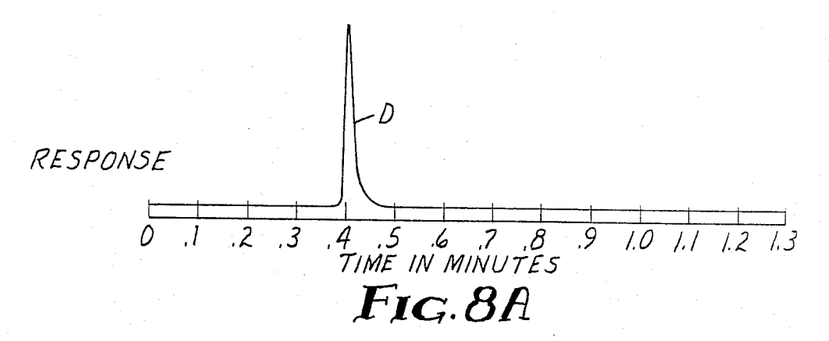
FIGS. 8A, 8B, and 8C are data acquisition system graphs for poly(vinyl p-toluene sulfonate, sodium salt) (SEE EXAMPLE 2).
Figure 8B:
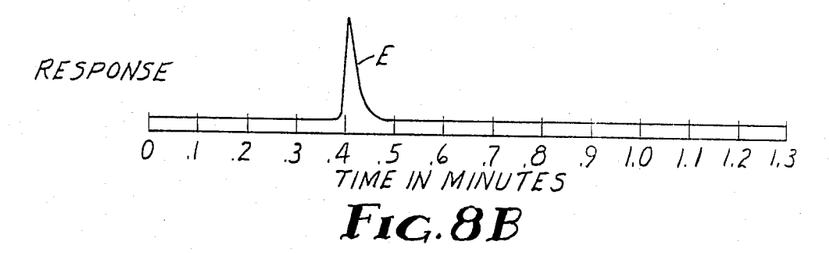
Figure 8C:
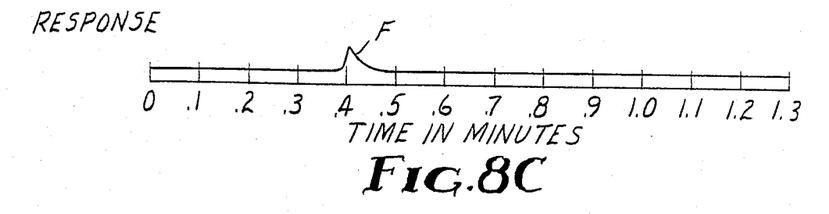

The process of EXAMPLE 1 was repeated except that poly(vinyl p-toluene sulfonate, sodium salt) dissolved in 1:1 water/methanol solution was deposited on the probe. Using the data acquisition system, the relative integrated response data and graphs obtained are as shown in FIGS. 8A, 8B, and 8C for carbon (D), hydrogen (E), and sulfur (F).

Various modifications and alterations of this invention will become apparent to those skilled in the art without departing from the scope and spirit of this invention, and it should be understood that this invention is not to be unduly limited to the illustrative embodiments set forth herein.

We claim:

1. A method of analysis of an inorganic or organic material comprising the steps of:
   (a) providing an immobilized sample of an inorganic or organic material in a gas atmosphere within a plasma cavity interfaced to an analytical device,
   (b) initiating a high frequency sustained radiation-induced excitation plasma within said plasma cavity spaced apart from said sample to provide a stable radiation baseline,
   (c) causing said plasma to elongate and encompass said sample for a length of time and at an energy level sufficient to pyrolyze said sample and cause it to emit radiation, and
   (d) analyzing the resulting atomic and molecular constituents or their emitted radiation.

2. The method according to claim 1 further comprising the step of initiating a second high frequency radiation-induced plasma which acts as a chaser plasma and is capable of moving said sample toward said excitation plasma.

3. The method according to claim 1 wherein said high frequency sustained radiation-induced plasma is selected from an inductively-coupled plasma, a direct current plasma, or a microwave-induced plasma.

4. A method of analysis of inorganic and organic materials comprising the steps of:
   (a) providing an immobilized sample of organic or inorganic material within a plasma cavity of a microwave-induced plasma detector having a variable power supply and an analytical device, said cavity having therein a gas atmosphere suitable for the generation and maintenance of a plasma at a pressure in the range of 1 to 760 mm of Hg,
   (b) initiating and sustaining a microwave-induced plasma in said plasma cavity in which said plasma is spaced apart from said sample by a distance of 0.1 to 10 cm, said power supply providing power to said plasma cavity in the range of 1 to 30 watts,
   (c) manipulating and controlling said power to supply sufficient power to said plasma cavity in a higher range to elongate said plasma to encompass said sample, said plasma being an excitation plasma.
   (d) maintaining said excitation plasma at said higher power range for a time period sufficient to pyrolyze said sample into atomic and molecular constituents and excite said atomic and molecular constituents so as to cause them to emit radiant energy,
   (e) analyzing the resulting atomic and molecular constituents of said sample or their emission spectra.

5. The method according to claim 4 wherein said microwave-induced plasma is spaced apart from said sample by a distance of 0.5 to 5 cm.

6. The method according to claim 4 wherein said gas atmosphere is selected from argon, helium, neon, krypton, radon, nitrogen, or oxygen.

7. The method according to claim 4 wherein said gas atmosphere is selected from helium and argon.

8. The method according to claim 4 wherein said power in said higher range is in the range of 50 to 500 watts.

9. The method according to claim 4 wherein said sample is volatile.

10. The method according to claim 4 wherein said gas pressure in said plasma cavity is in the range of 1 to 5 mm of Hg.

11. The method according to claim 4 wherein said pyrolysis time is in the range of 0.01 to 300 sec.

12. The method according to claim 4 wherein said emission spectral analysis is obtained by a spectrometric device.

13. The method according to claim 4 wherein said sample is non-volatile.

14. The method according to claim 4 further comprising the step of initiating a second microwave-induced plasma which acts as a chaser plasma and is capable of moving said sample toward said excitation plasma.

15. The method according to claim 14 wherein said plasmas are caused to fuse into one plasma.

16. In an apparatus for analyzing a sample of an inorganic or organic material, wherein said sample is in a discharge tube, having an inside wall, within a plasma cavity interfaced to an analytical device and a high frequency sustained radiation-induced excitation plasma is initiated and sustained in said plasma cavity by means of power applied to an inert gas atmosphere in said discharge tube, which plasma is capable of causing said sample to pyrolyze and emit radiation, and said analytical dvice comprises means for detecting said emitted radiation or resulting atomic and molecular constituents,
   the improvement comprising:
   means for fixing said sample at a position spaced apart from said plasma, and
   means for elongating said plasma so as to cause it to encompass said sample,
   wherein said detecting means is located to directly detect said emitted radiation or resulting atomic or molecular constituents in the proximity of said sample position whereby the need for a carrier gas is obviated.

17. The apparatus according to claim 16 wherein said means for immobilizing said sample comprises:
   means for moving said sample to, and fixing said sample at, a specific site in the interior of said discharge tube.

18. The apparatus according to claim 16 wherein said means for immobilizing said sample comprises:
   means for containing said sample on the inside wall of said discharge tube.

19. The apparatus according to claim 16 wherein said means for elongating said plasma comprises:
   means for changing the power applied to said plasma.

20. The apparatus according to claim 16 wherein said means for elongating said plasma comprises:
   means for decreasing the gas pressure inside said discharge tube.

* * * * *